United States Patent [19]
Jaouen et al.

[11] Patent Number: 5,863,911
[45] Date of Patent: Jan. 26, 1999

[54] DIARYLETHYLENE METALLOCENE DERIVATIVES, THEIR PROCESSES OF PREPARATION AND PHARMACEUTICAL COMPOSITIONS CONTAINING SAID DERIVATIVES

[75] Inventors: Gérard Jaouen, L'Hay-les-Roses; Siden Top, Lisses, both of France

[73] Assignee: Modelisation et Mise au Point de Molecules Medicinales, Paris, France

[21] Appl. No.: 908,106

[22] Filed: Aug. 11, 1997

Related U.S. Application Data

[63] Continuation of Ser. No. 817,223, filed as PCT/FR95/01323, Oct. 11, 1995, abandoned.

[30] Foreign Application Priority Data

Oct. 12, 1994 [FR] France .................................. 94 12151

[51] Int. Cl.⁶ .......................... A61K 31/555; C07F 17/00
[52] U.S. Cl. .......................... 514/184; 514/492; 514/501; 514/502; 544/64; 546/11; 548/402; 556/43; 556/53; 556/58; 556/143; 556/144; 556/145; 556/136
[58] Field of Search .................................. 556/43, 53, 58, 556/136, 143, 144, 145; 514/492, 501, 502, 184; 548/402; 546/11; 544/64

[56] References Cited

U.S. PATENT DOCUMENTS

| | | | |
|---|---|---|---|
| 3,960,911 | 6/1976 | Suschitzky et al. | ............. 260/439 CY |
| 5,082,539 | 1/1992 | Saji et al. | ................................. 205/162 |

FOREIGN PATENT DOCUMENTS

| | | |
|---|---|---|
| 153 636 | 9/1985 | European Pat. Off. . |
| 2 352 825 | 12/1977 | France . |
| 96/11935 | 4/1996 | WIPO . |

OTHER PUBLICATIONS

Suprabhat Ray et al., "An X–ray Crystallographic Study of the Nonsteroidal Contraceptive Agent Centchroman", *J. Med. Chem.*, 1994, vol. 37, No. 5, pp. 696–700.

V. Craig Jordan et al., "Endocrine Pharmacology of Antiestrogens as Antitumor Agents", Department of Human Oncology, University of Wisconsin Clinical Cancer Center, Madison, Wisconsin, Nov. 1990, vol. 11, No. 4, pp. 578–611.

Jean–Christophe Doré et al., "Multivariate Analysis by the Minimum Spanning Tree Method of the Structural Determinants of Diphenylethylenes and Triphenylacrylonitriles Implicated in Estrogen Receptor Binding, Protein Kinase C Activity, and $MCF_7$ Cell Proliferation", *J. Med. Chem.*, 1992, vol. 35, No. 3, pp. 573–583.

Philip R. Kym et al., "Molecular Structures, Conformational Analysis, and Preferential Modes of Binding of 3–Aroyl–2–arylbenzo[β]thiophene Estrogen Receptor Ligands: LY117018 and Aryl Azide Photoaffinity Labeling Analogs", *J. Med. Chem.*, 1993, vol. 36, No. 24, pp. 3910–3922.

Gérard Jaouen et al., "Bioorganometallic Chemistry: A Future Direction for Transition Metal Organometallic Chemistry?", *Acc. Chem. Res.*, 1993, vol. 26, No. 7, pp. 361–369.

Douglas M. Wolf et al., "Drug Resistance to Tamoxifen During Breast Cancer Therapy", *Breast Cancer Research and Treatment*, 1993, 27, pp. 27–40.

*Primary Examiner*—Porfirio Nazario-Gonzalez
*Attorney, Agent, or Firm*—Bell Seltzer Intellectual Property Law Group of Alston & Bird LLP

[57] ABSTRACT

Diarylethylene metallocene derivatives, processes for preparing the same and pharmaceutical compositions which contain the derivatives are disclosed. The compounds of the invention can exhibit anti-tumor activity, and can be particularly useful in the treatment of estrogen-dependent cancers.

29 Claims, 2 Drawing Sheets

DIARYLETHYLENE METALLOCENE DERIVATIVES, THEIR PROCESSES OF PREPARATION AND PHARMACEUTICAL COMPOSITIONS CONTAINING SAID DERIVATIVES

This application is a continuation of application Ser. No. 08/817,223, filed as PCT/FR95/01323, Oct. 11, 1995, now abandoned.

The present Invention relates to diarylethylene metallocene derivatives, to their processes of preparation and to pharmaceutical compositions containing said derivatives.

Some classes of triarylethylene derivatives have representatives, such as tamoxifen or nafoxidine, which combine weak estrogenic properties with marked antiestrogenic properties which are the basis of their use as oral contraceptives (Ray et al., J. Med. Chem., 1994, 37, 696), as inducers of ovulation and in particular as antitumor agents (Jordan and Murphy, Edocr. Rev., 1990, 11, 578; Dore et al., J. Med. Chem., 1992, 35, 573; Kym et al., J. Med. Chem., 1993, 36, 3910).

This duality of weak estrogenic and pronounced antiestrogenic properties doubtless results from the presence of two distinct functional components in the structure of these compounds. It concerns, on the one hand, an entity of trans-stilbene type which simulates the structure of the synthetic estrogen, diethylstilbestrol, and, on the other hand, an additional polar residue composed, for example, of a group of the (ω-tert-aminoalkoxy)phenyl type which interferes with the initiation of the estrogenic activity and is responsible for the antiestrogenic activity.

The hypothesis of the presence of coordinating acidic $Zn^{++}$ in the region of the association site of the hormone has recently been advanced to explain this behavior (Jaouen et al., Acc. Chem. Res., 1993, 26, 361).

Whatever the nature of the molecular process involved, tamoxifen is widely used as adjuvant therapy in the control of cancers of the breast responding positively to analysis of estradiol receptors. This molecule has a positive effect on the survival of the patients and is moreover well tolerated.

However, as the action of tamoxifen is tumoristatic rather than tumoricidal, its use in this indication generally justifies prolonged administration, during which some patients develop resistance to the treatment (Wolf and Jordan, Breast Cancer Res. Treat., 1993, 27, 27). In extreme cases, some tumors of the breast and of the endometrium end up by growing by stimulation with tamoxifen.

For this reason, the problem is posed of developing new molecules which possess antitumor properties and which are capable of replacing the triarylethylene antiestrogens of the Prior Art, in particular tamoxifen, in their antitumor applications, such as the treatment of estrogen-dependant cancers of the breast.

The problem is solved by the present Invention which provides a new family of compounds capable of acting advantageously as substitutes for the triarylethylene antiestrogens of the Prior Art, in particular tamoxifen, because they exhibit an antitumor activity greater than that of the latter, processes for the preparation of these new compounds and pharmaceutical compositions containing said compounds.

The subject of the present Invention is therefore compounds of general formula (I):

wherein:

the $—O(CH_2)nZ$ group is in the meta or para position with respect to the $—CR_3=CR_4R_5$ group, n represents an integer of between 2 and 10, Z represents a basic or polar ligand chosen from $-NR_1R_2$ groups wherein $R_1$ and $R_2$, which are identical or different, represent a $C_1$ to $C_6$ alkyl group optionally substituted by one or a number of halogen atoms, heterocyclic groups containing a nitrogen atom or $-OR_1, -SR_1, -SOR_1$ or $-SO_2R_1$ groups wherein $R_1$ has the same meaning as above, and wherein:

either $R_3$ represents a phenyl group optionally substituted by one or a number of hydrogen atoms or halogen atoms or hydroxyl groups or $C_1$ to $C_3$ alkyl or alkoxy groups and $R_5$ represents a metallocene group, whereas $R_4$ represents a hydrogen atom or a halogen atom or an $NO_2$ group or a chloroethyl group or a CN group or alternatively a $C_1$ to $C_3$ alkyl group, the end carbon of which can optionally be bonded to the carbon situated at the 2 position of the phenyl group of $R_3$, or $R_3$ represents a metallocene group and $R_5$ represents a phenyl group optionally substituted by one or a number of hydrogen atoms or halogen atoms or hydroxyl groups or $C_1$ to $C_3$ alkyl or alkoxy groups, whereas $R_4$ represents a hydrogen atom or a halogen atom or an $NO_2$ group or a chloroethyl group or a CN group or alternatively a $C_1$ to $C_3$ alkyl group, in all their stereoisomeric forms and their salts.

Unexpectedly, the Inventors have in fact discovered that the attachment, to the same skeleton, of an antiestrogenic component and of a metallocene entity results in compounds which have marked tumoristatic and tumoricidal properties superior to those of the antiestrogens of the Prior Art and, for this reason, are capable of being used as antitumor agents, in particular in the treatment of estrogen-dependant cancers of the breast.

In the preceding and the following, the expression "$C_1$ to $C_6$ alkyl" denotes any linear or branched alkyl group having no more than 6 carbon atoms, such as, for example, the methyl, ethyl, propyl, butyl, isopropyl or alternatively isobutyl radicals.

Similarly, the expression "$C_1$ to $C_3$ alkyl" denotes any linear or branched alkyl group having no more than 3 carbon atoms.

The present Application is targeted at denoting, by "$C_1$ to $C_3$ alkoxy", any alkoxy group having no more than 3 carbon atoms, such as, for example, a methoxy, ethoxy, propoxy or isopropoxy group.

The expression "heterocyclic group containing a nitrogen atom" denotes a nitrogenous heterocycle comprising no more than 6 atoms in the ring, such as, for example, an N-piperidino, N-morpholino or N-pyrrolidino group.

The expression "halogen" denotes chlorine, fluorine, bromine or iodine.

In a preferred embodiment of the Invention, the metallocene group corresponds to the general formula (II):

(II)

wherein M represents a metal atom from Group VIII of the Periodic Classification of the chemical elements, it being possible for said atom optionally to be in an oxidized form.

In another embodiment of the Invention, the metallocene group corresponds to the general formula (III):

(III)

wherein:

M represents a metal atom chosen from titanium, vanadium, niobium, hafnium or molybdenum, and X represents a halogen atom chosen from chlorine, bromine or iodine.

The subject of the Invention is more particularly the compounds as defined above, wherein they correspond to the specific formula (I-a):

(I-a)

wherein:

the —O(CH$_2$)$_2$Z group is in the para position with respect to the —CR$_3$=CR$_4$R$_5$ group,

Z represents an —NR$_1$R$_2$ group wherein R$_1$ and R$_2$, which are identical or different, represent a methyl group or an ethyl group or alternatively Z represents an N-pyrrolidino group, R$_3$ represents a phenyl group optionally substituted by a hydroxyl group or by a methoxy group, R$_4$ represents a hydrogen atom or a halogen atom or an NO$_2$ group or a chloroethyl group or a CN group or alternatively an ethyl group, and

M represents a metal atom chosen from iron, ruthenium or osmium, optionally in its oxidized form.

These compounds can form isomers so that, in the following, "trans" isomers will denote the compounds of formula (I-a) exhibiting the configuration below:

(trans)

wherein the R$_3$ group and the metallocene group are in the "trans" position with respect to one another on either side of the olefin bond, whereas "cis" isomers will denote the metallocene compounds exhibiting the configuration below:

(cis)

wherein the R$_3$ group and the metallocene group are in the "cis" position with respect to one another on either side of the olefin bond.

Preference is given in particular, among the compounds of formula (I-a), to those corresponding to the specific formula (I-a1) wherein R$_1$ and R$_2$ represent a methyl group, R$_3$ represents a phenyl group substituted in the para position by a hydroxyl group and R$_4$ represents an ethyl group.

The specific formula (I-a1) is represented below in the "trans" configuration:

(I-a1)

Preferentially, M represents an iron atom and the corresponding metallocene compound is 1-[4-(2-dimethylaminoethoxy)phenyl]-1-(4-hydroxyphenyl)-2-ferrocenyl-1-butene.

In a particularly preferred way, the metallocene compound is the "trans" isomer of 1-[4-(2-dimethylaminoethoxy)phenyl]-1-(4-hydroxyphenyl)-2-ferrocenyl-1-butene.

Preference is also given, among the compounds of formula (I-a), to the compounds corresponding to the specific formula (I-a2) wherein $R_1$ and $R_2$ represent a methyl group, $R_3$ represents a phenyl group and $R_4$ represents an ethyl group.

The specific formula (I-a2) is represented below in the "trans" configuration:

(I-a2)

Preferably, M represents an iron atom and the corresponding metallocene compound is 1-[4-(2-dimethylaminoethoxy)phenyl]-1-phenyl-2-ferrocenyl-1-butene.

The subject of the Invention is also more particularly the compounds corresponding to the general Formula (I) wherein, in this formula (I): the —O(CH$_2$)$_n$Z group is in the para position with respect to the —CR$_3$=CR$_4$R$_5$ group, n is equal to 2 and Z represents an N-pyrrolidino group, $R_3$ represents a phenyl group substituted in the para position by a hydroxyl or $C_1$ to $C_3$ alkoxy group, whereas $R_4$ represents a $C_2$ alkyl group, the end carbon of which is bonded to the carbon situated in the 2 position of the phenyl group of $R_3$, M represents a metal atom chosen from iron, ruthenium or osmium, optionally in its oxidized form.

These compounds correspond to the specific formula (I-b):

(I-b)

wherein $R_6$ represents a hydrogen atom or a $C_1$ to $C_3$ alkyl group.

In accordance with the invention, the compounds of general formula (I) can be prepared according to a process which comprises:

a) reacting a compound of general formula (IV):

(IV)

wherein:

the —O(CH$_2$)$_n$Z group is in the meta or para position with respect to the —CR$_3$=CR$_4$R$_5$ group, n represents an integer of between 2 and 10, Z represents a basic or polar ligand chosen from —NR$_1$R$_2$ groups wherein $R_1$ and $R_2$, which are identical or different, represent a $C_1$ to $C_6$ alkyl group optionally substituted by one or a number of halogen atoms, heterocyclic groups containing a nitrogen atom or —OR$_1$, —SR$_1$, —SOR$_1$ or —SO$_2$R$_1$ groups wherein $R_1$ has the same meaning as above, and wherein:

either $R_3$ represents a phenyl group optionally substituted by one or a number of hydrogen atoms or halogen atoms or hydroxyl groups or $C_1$ to $C_3$ alkyl or alkoxy groups and $R_5$ represents a bromine atom, whereas $R_4$ represents a hydrogen atom or a halogen atom or an NO$_2$ group or a chloroethyl group or a CN group or alternatively a $C_1$ to $C_3$ alkyl group, the end carbon of which can optionally be bonded to the carbon situated at the 2 position of the phenyl group of $R_3$, or $R_3$ represents a bromine atom and $R_5$ represents a phenyl group optionally substituted by one or a number of hydrogen atoms or halogen atoms or hydroxyl groups or $C_1$ to $C_3$ alkyl or alkoxy groups, whereas $R_4$ represents a hydrogen atom or a halogen atom or an NO$_2$ group or a chloroethyl group or a CN group or alternatively a $C_1$ to $C_3$ alkyl group, with a cyclopentadienyl metal salt, in order to substitute the bromine atom by a cyclopentadiene group;

b) reacting the compound obtained in Stage a) with a strong base, in order to form a cyclopentadienyl anion, c) reacting the compound obtained in Stage b) with an organometallic compound of formula: Cp—M—(CO)$_2$—X, wherein Cp represents a cyclopentadiene group, M represents a metal atom from Group VIII of the Periodic Classification of the chemical elements and X represents a halogen atom chosen from chlorine, bromine or iodine, or with an organometallic compound of formula: Cp—M—X$_m$, wherein Cp and X have the same meaning as above, M represents a metal atom chosen from titanium, vanadium, niobium, hafnium or molybdenum and m is an integer equal to 3 or 4.

The compounds of general formula (IV) can be prepared according to the processes which have been provided in the Prior Art for the synthesis of triarylethylene antiestrogens (Cur. Med. Chem., 1994, 1, 61–104).

A cyclopentadienyl metal salt which is suitable for the implementation of Stage a) of this process is represented by sodium cyclopentadienylide.

The strong base which is useful for the implementation of Stage b) can be, for example, NaH or NaNH$_2$.

Although the compounds of specific formula (I-a1) can be prepared according to the preparation process described above, another subject of the Invention is a specific process for the preparation of the compounds of formula (I-a1), which comprises:

a) subjecting a metallocene ester of formula (V):

wherein M represents a metal atom chosen from iron, ruthenium or osmium, to an addition reaction with the organolithium compound $CH_3—O—C_6H_4—Li$ or an organomagnesium compound of formula: $CH_3—O—C_6H_4—MgX$, wherein X represents a chlorine, bromine or iodine atom, which results in the formation of an intermediate alcohol, followed by a dehydration reaction of said alcohol, b) subjecting the compound obtained in Stage a) to a demethylation reaction, c) subjecting the compound obtained in Stage b) to an alkylation reaction with sodium ethoxide and the hydrochloride of 2-dimethylaminoethyl chloride.

A mixture of the two "cis" and "trans" isomers of a compound of formula (I-a1) is thus obtained.

The dehydration of the intermediate alcohol can advantageously be carried out by the action of a strong acid, such as hydrochloric acid.

The demethylation reaction can advantageously be carried out by the action of boron tribromide in the presence of an appropriate solvent, such as, for example, dichloromethane.

In a preferred embodiment of the process in accordance with the Invention, this process comprises the prior preparation of the metallocene ester of formula (V) by esterification of the corresponding metallocenylacetic acid, followed by an alkylation reaction of the carbon in the position α to the metallocenyl ring of said ester.

The metallocenylacetic acid can be esterified by means of a strong base, such as potassium tert-butoxide (t-BuOK).

A suitable alkylating reagent is represented by iodoethane. This alkylation is advantageously carried out in the presence of a strong base, such as, for example, t-BuOK or sodium or potassium hexamethyldisilazanide, and of an appropriate solvent, such as, for example, dimethyl sulfoxide (DMSO).

The metallocenylacetic acid can be prepared according to the method described in the literature (Lednicer et al., J. Org. Chem., 1958, 23, 653), which comprises the reaction of a metallocenylmethyltrimethylammonium iodide with potassium cyanide, in order to obtain the corresponding metallocenylacetonitrile, and then the hydrolysis of the latter.

Insofar as the preparation of a metallocene derivative of formula (I-a1) according to this process always results in the production of the two "cis" and "trans" isomers of said derivative and as generally only one of the two isomers, namely the "trans" isomer, exhibits pronounced antiestrogenic properties, it can be advantageous to proceed to a separation of the two isomers obtained on conclusion of abovementioned Stage c).

In accordance with the Invention, the specific process for the preparation of the compounds of formula (I-a1) in addition comprises a stage of separation of the "cis" and "trans" isomers of these compounds.

This separation can advantageously be carried out by fractional crystallization. It is, however, possible to use other techniques of the Prior Art, such as, for example, thin-layer chromatography using an appropriate eluent.

Although the compounds of specific formula (I-a2) can also be obtained by the process for the preparation of the compounds of general formula (I), another subject of the Invention is a specific process for the preparation of these compounds of specific formula (I-a2) which comprises:

a) reacting a metallocenic acid chloride of formula (VI):

wherein M represents a metal atom chosen from iron, ruthenium or osmium, with diphenylzinc, in order to substitute the chlorine atom by a phenyl group, b) subjecting the compound obtained in Stage a) to an addition reaction with the organolithium compound $(CH_3)_2—N—(CH_2)_2—O—C_6H_4—Li$ or an organomagnesium compound of formula: $(CH_3)_2—N—(CH_2)_2—O—C_6H_4—MgX$, wherein x represents a halogen atom chosen from chlorine, bromine or iodine, which results in the formation of an intermediate alcohol, followed by a dehydration reaction of said alcohol.

A mixture of the two "cis" and "trans" isomers of a compound of formula (I-a2) is thus obtained.

The metallocenic acid chloride can be obtained by the reaction of phosphorus trichloride or pentachloride or of thionyl chloride or alternatively of triphosgene with the corresponding 2-metallocenylbutanoic acid.

The dehydration of the intermediate alcohol can be carried out by the action of a strong acid, such as hydrochloric acid.

The preparation of a compound of formula (I-a2) according to this process always results in the production of the two "cis" and "trans" isomers of said compound, so that it comprises in addition a stage of separation of these "cis" and "trans" isomers, which separation can be carried out, for example, by fractional crystallization.

Another subject of the present Invention is a specific process for the preparation of the compounds of formula (I-b), which comprises:

a) reacting a tetralone of formula (VII):

wherein $R_6$ represents a hydrogen atom or a $C_1$ to $C_3$ alkyl group, with the organolithium compound or an organomagnesium compound of formula:

wherein X represents a halogen atom chosen from chlorine, bromine or iodine, which results in the formation of an intermediate alcohol, followed by a dehydration reaction of said alcohol;

b) subjecting the compound obtained in Stage a) to a bromination reaction, in order to obtain the compound of formula (VIII):

(VIII)

c) subjecting the compound of formula (VIII) thus obtained to a coupling reaction with an organometallic compound of formula: Cp—M—($C_5H_4$)—Y, wherein Cp represents a cyclopentadiene group, M represents a metal atom chosen from iron, ruthenium or osmium and Y represents a lithium atom, a copper atom, an $SnBu_3$ group or an HgCl group.

The bromination reaction to which the compound of formula (VIII) is subjected can be carried out with hydrobromic acid in the presence of an appropriate solvent, such as, for example, pyridine.

The products of general formula (I) and their addition salts with acids acceptable from the pharmacological viewpoint can be administered to man as medicaments, alone or in the form of pharmaceutical compositions which make possible enteral or parenteral application and which contain, as active constituent, an effective dose of at least one product of formula (I) or an acid addition salt of such a compound with, in addition, inoffensive excipients and additives taken from those commonly used in pharmaceuticals.

The products of general formula (I) and their salts find, due to their tumoristatic and tumoricidal properties, application in the preparation of medicaments with an antitumor purpose, in particular in the treatment of estrogen-dependant cancers of the breast.

In addition to the preceding arrangements, the Invention also comprises other arrangements which will emerge from the following description, given by way of examples, and with reference to the appended drawings wherein.

It should be clearly understood, however, that these examples are given by way of illustration of the Invention and do not constitute in any way a limitation thereof.

EXAMPLE 1

Preparation of the "trans" and "cis" isomers of 1-[4-(2-dimethylaminoethoxy)phenyl]-1-(4-hydroxyphenyl)-2-ferrocenyl-1-butene 1.1: Preparation of ferrocenylacetonitrile 8.00 g (20.8 mmol) of ferrocenylmethyltrimethylammonium iodide (Strem) and 8 g of KCN (123 mmol) are dissolved in 80 ml of water. The mixture is placed in a round-bottomed flask surmounted by a reflux condenser. The mixture is heated at reflux for 2 hours and is then allowed to cool to room temperature. The product is extracted with 3 times 40 ml of ethyl ether. The organic phase is washed first with 2 times 30 ml of water and then dried over magnesium sulfate. After filtration and evaporation, 4.1 g of ferrocenylacetonitrile are collected.

Chemical formula: $C_{12}H_{11}NFe$
Mass: 225
Yield: 87.7%.

1.2: Preparation of ferrocenylacetic acid 4.10 g (18.2 mmol) of ferrocenylacetonitrile are dissolved in 80 ml of ethanol. 10.08 g of KOH (180 mmol) are dissolved in 80 ml of water. The potassium hydroxide solution is poured into the first solution and the mixture is brought to reflux for 4 hours. The reaction mixture is concentrated in order to remove most of the ethanol. The product is extracted with 3 times 30 ml of ether. The aqueous phase is acidified with hydrochloric acid to a pH of 1 and is again extracted with 4 times 50 ml of ethyl ether. The organic phases are combined, dried over magnesium sulfate, filtered and then evaporated. 4.20 g of ferrocenylacetic acid are obtained in the form of a yellow solid.

Chemical formula: $C_{12}H_{12}O_2Fe$
Mass: 244
Yield: 94.5%

$^1$H NMR (200 MHz, $CDCl_3$): δ 4.23 (m, 2H, substituted Cp), 4.15 (s, 7H, Cp and substituted Cp), 3.42 (s, 2H, $CH_2$).

1.3: Preparation of ethyl ferrocenylacetate 2.00 g (8.2 mmol) of ferrocenylacetic acid are dissolved in 50 ml of ethanol. 0.5 ml of concentrated sulfuric acid is added. The mixture is brought to reflux for 1 hour. After cooling, the reaction mixture is poured into 100 ml of ice-cold water. The product is extracted with 3 times 40 ml of ether. The ethereal phase is first washed with water (2 times 40 ml) and then dried over magnesium sulfate, filtered and evaporated. 2.22 g of ethyl ferrocenylacetate are obtained. The yield of the reaction is 100%.

Chemical formula: $C_{14}H_{16}O_2Fe$
Mass: 272

$^1$H NMR (200 MHz, $CDCl_3$): δ 4.23 (m, 2H, substituted Cp), 4.18 (m, 2H, O—$CH_2$), 4.14 (s, 5H, Cp), 4.13 (m, 2H, substituted Cp), 3.34 (s, 2H, Cp—$CH_2$), 1.31 (t, 3H, J=7.12 Hz, Me).

1.4: Preparation of ethyl 2-ethyl-2-ferrocenylacetate 2.22 g (8.2 mmol) of ethyl ferrocenylacetate are dissolved in 25 ml of anhydrous DMSO under an argon atmosphere. 1.01 g (9 mmol) of t-BuOK are added. After stirring for 5 minutes, 1.5 g (9.6 mmol) of iodoethane are rapidly added. Stirring is continued for 2 minutes and then the reaction mixture is poured into 100 ml of ice-cold water. The product is extracted with 3 times 50 ml of ether. The ethereal phase is washed twice with 50 ml of water, dried over magnesium sulfate, filtered and then evaporated. The crude product obtained is chromatographed on $60GF_{254}$ (Merck 7730) silica gel plates with a thickness of 1 mm with a 1/9 ether/pentane mixture as eluent.

1.16 g of ethyl 2-ethyl-2-ferrocenylacetate are obtained ($R_f$=0.6) with a yield of 47%.

Chemical formula: $C_{16}H_{20}O_2Fe$
Mass: 300

$^1$H NMR (200 MHz, $CDCl_3$): δ4.23 (m, 2H, substituted Cp), 4.16 (m, 2H, O—$CH_2$), 4.13 (s, 5H, Cp), 4.12 (m, 2H, substituted Cp), 3.19 (m, 1H, Fc—CH—), 1.77 (m, 2H, Fc—CH—CH$_2$), 1.35 (T, 3H, J=7.14 Hz, O—CH$_2$—CH$_3$), 0.92 (t, 3H, J=7.38 Hz, CH—CH$_2$—CH$_3$).

1.5: Preparation of 1,1-bis(4-methoxyphenyl)-2-ferrocenyl-1-butene 1.20 g (5.5 mmol) of 4-iodoanisole are dissolved in 20 ml of anhydrous ether under an argon atmosphere. The solution is cooled to 0° C. and then 2.9 ml (4.6 mmol) of a 1.6M n-butyllithium solution are added dropwise. After complete addition, the mixture is maintained at 0° C. for 15 minutes. A solution of ethyl 2-ethyl-2-ferrocenylacetate (0.69 g, 2.3 mmol) dissolved in 10 ml of anhydrous ether is placed in the dropping funnel. The latter solution is added dropwise to the first solution, the temperature being maintained at 0° C. Stirring is maintained for 30 minutes at 0° C. and 2 hours at room temperature. A 1N hydrochloric acid solution is then added to a pH of 1 and the reaction mixture is heated at reflux for 4 hours. After cooling, the product is extracted with ether. The ethereal phase is first washed with water, dried over magnesium sulfate, filtered and then evaporated. The crude product obtained is chromatographed on 60GF$_{254}$ silica gel plates with a 1/9 ether/pentane mixture as eluent. 0.65 g of the desired compound is obtained (R$_f$=0.45) with a yield of 62.5%.

Chemical formula: C$_{28}$H$_{28}$O$_2$Fe
Mass: 452

$^1$H NMR (200 MHz, CDCl$_3$): δ7.12 and 6.16 (dd, 4H, J=8.4 Hz, C$_6$H$_4$), 6.98 and 6.87 (dd, 4H, J=8.4 Hz, C$_6$H$_4$), 4.14 (s, 5H, Cp), 4.10 (m, 2H, substituted Cp), 3.95 (m, 2H, substituted Cp), 3.82 and 3.78 (s, s, 3H, 3H, O—Me),2.56 (q, 2H, J=7.4 Hz, —CH$_2$—CH$_3$), 1.02 (t, 3H, J=7.3 Hz, —CH$_2$—CH$_3$).

1.6 : Preparation of 1,1-bis(4-hydroxyphenyl)-2-ferrocenyl-1-butene 0.55 g (1.28 mmol) of 1,1-bis(4-methoxyphenyl)-2-ferrocenyl-1-butene is dissolved in 5 ml of dichloromethane under an argon atmosphere. The solution is cooled to −78° C. and then 0.3 ml (2.84 mmol) of BBr$_3$ is added. After complete addition, the cold bath is removed and stirring is maintained for 30 minutes. The reaction mixture is then poured into ice-cold water. After stirring for 10 minutes, NaCl is added to saturation and the product is extracted with dichloromethane (4 times 40 ml). The organic phase is first washed with water, dried over magnesium sulfate, filtered and then evaporated. The crude product obtained is chromatographed on 60GF$_{254}$ silica gel plates with a 3/2 ether/pentane mixture as eluent.

0.43 g of the desired compound is obtained (R$_f$=0.4; yield=79%).

Chemical formula: C$_{26}$H$_{24}$O$_2$Fe
Mass: 424

$^1$H NMR (200 MHz, CDCl$_3$):δ 7.07 and 6.68 (d, d, 4H, J=8.6 Hz, C$_6$H$_4$), 6.92 and 6.80 (d, d, 4H, J=8.5 Hz, C$_6$H$_4$), 4.88 and 4.42 (s, s, H, H, 2 OH), 4.11 (s, 5H, Cp), 4.08 (m, 2H, substituted Cp), 3.91 (m, 2H, substituted Cp), 2.58 (q, 2H, J=7.5 Hz, —CH$_2$—CH$_3$), 1.02 (t, 3H, J=7.5 Hz, —CH$_2$—CH$_3$).

1.7: Production of the "trans" and "cis" isomers of 1-[4-(2-dimethylaminoethoxy)phenyl]-1-(4-hydroxyphenyl)-2-ferrocenyl-1-butene A sodium ethoxide solution is first prepared by reacting 0.120 g (5.2 mmol) of sodium with 20 ml of ethanol. 0.450 g (1.06 mmol) of 1,1-bis(4-hydroxyphenyl)-2-ferrocenyl-1-butene, dissolved in 10 ml of ethanol, is then added to this solution. After stirring for 1 hour at 80° C., 0.302 g (2.1 mmol) of 2-dimethylaminoethyl chloride hydrochloride is added and the mixture is heated at reflux for 3 hours. The solution is then allowed to cool to room temperature.

Hydrolysis is carried out with 100 ml of water and the product is extracted with ether (4 times 50 ml). The organic phase is first washed with water, dried over magnesium sulfate, filtered and then evaporated. The crude product obtained is chromatographed on 60GF$_{254}$ silica gel plates with a 1/9 (C$_2$H$_5$)$_3$N/chloroform mixture as eluent.

0.280 g of the mixture of the "trans" isomer and of the "cis" isomer of 1-[4-(2-dimethylaminoethoxy)phenyl]-1-(4-hydroxyphenyl)-2-ferrocenyl-1-butene is first obtained (Yield=53%).

The second, more polar, fraction corresponds to 1,1-bis [4-(2-dimethylaminoethoxy)phenyl]-2-ferrocenyl-1-butene (0.050 g; Yield=9.5%).

1.8: Separation of the "trans" and "cis" isomers of 1-[4-(2-dimethylaminoethoxy)phenyl]-1-(4-hydroxyphenyl)-2-ferrocenyl-1-butene The mixture of the two isomers obtained above is dissolved in an ether/hexane (5/1) mixture and the solution obtained is left in a refrigerator overnight.

As the solubility in ether of the "cis" isomer is lower than that of the "tans" isomer, the "cis" isomer crystallizes first after gentle evaporation of the solvent. The crystals of the "cis" isomer are isolated and the mother liquors are recooled in the freezer compartment (−15° C.) of the refrigerator for one day. The "trans" isomer then crystallizes in its turn in the form of fine needles.

EXAMPLE 2

Characterization of the "trans" and "cis" isomers of 1-[4-(2-dimethylaminoethoxy)phenyl]-1-(4-hydroxyphenyl)-2-ferrocenyl-1-butene 2.1: Chemical formula and molar mass
Chemical formula: C$_{30}$H$_{33}$O$_2$NFe
Molar mass: 495.4

2.2: $^1$H NMR spectrometric data

The $^1$H NMR spectra of the two "trans" and "cis" isomers were recorded on a Bruker AC200 Mz spectrometer in d$_6$-DMSO (Janssen), because this solvent does not bring about isomerization of the two isomers.

The $^1$H NMR values of the two isomers are as follows:
"Trans" isomer:

δ: 9.34 (s, 1H, OH), 6.97 and 6.71 (d, d, 4H, J =8.7 Hz, C$_6$H$_4$—OH), 6.89 and 6.80 (d, d, 4H, J =8.5 Hz, C$_6$H$_4$—CH$_2$), 4.11 (s, 5H, Cp), 4.07 (m, 2H, substituted Cp), 3.99 (t, 2H, J=6.0 Hz, O—CH$_2$), 3.80 (m, 2H, substituted Cp), 2.60 (t, 2H, J=6.0 Hz, N—CH$_2$), 2.49 (masked by the DMSO signal, 2H, —CH$_2$—CH$_3$), 2.20 (s, 6H, NMe$_2$), 0.98 (t, 3H, J=7.3 Hz, —CH$_2$—CH$_3$)

"Cis" isomer:

δ: 9.29 (s, 1H, OH), 7.08 and 6.89 (d, d, 4H, J=8.5 Hz, C$_6$H$_4$—OCH$_2$), 6.80 and 6.63 (d, d, 4H, J=8.4 Hz, C$_6$H$_4$—OH), 4.11 (s, 5H, Cp), 4.08 (m, 2H, (t, 2H, J=6.0 Hz, N—CH$_2$), 2.49 (masked by the DMSO signal, 2H, —CH$_2$—CH$_3$), 2.23 (s, 6H, NMe$_2$), 0.98 (t, 3H, J=7.3 Hz, —CH$_2$—CH$_3$).

2.3: Melting points

The melting points of the "trans" and "cis" isomers were determined using a Kofler bench. They are respectively 93°–94° C. for the "trans" isomer and 181° C. for the "cis" isomer.

EXAMPLE 3

Cytotoxic activity of the "trans" and "cis" isomers of 1-[4-(2-dimethylaminoethoxy)phenyl]-1-(4-hydroxyphenyl)-2-ferrocenyl-1-butene The evaluation of the cytotoxicity of the "trans" and "cis" isomers of 1-[4-(2-dimethylaminoethoxy)phenyl]-1-(4-hydroxyphenyl)-2-ferrocenyl-1-butene has formed the subject of tests on human cell lines derived from a plural effusion from a mammary adenocarcinoma (MCF-7 ATCC HTB line) and one of its variants (MCF-7P line).

These cells were precultured in Dulbecco's MEM medium, to which has been added 10% fetal calf serum, in a moist atmosphere (90% relative humidity) comprising 5% $CO_2$. In the exponential growth phase, these cells were trypsinated and subcultured in 24-well plates, the wells having a capacity of 1 ml, in the proportion of $2 \times 10^5$ cells per well.

After incubating for 3 days, the test compounds were added at the appropriate doses and the plates were incubated for 5 days.

On conclusion of this incubation, the cell viability of the cultures was determined using the so-called "MTT" test which comprises the addition to each well of 20 µl of a solution containing 5 mg of 3-(4,5-dimethylthiazol-2-yl)-2, 5-diphenyltetrazolium bromide (MTT) in 1 ml of PBS buffer, followed by allowing the plates to incubate for 1 hour at 37° C. under atmospheric conditions identical to those defined above. MTT is metabolized in living cells into an insoluble blue compound (formazan).

On conclusion of this incubation, the wells are washed using PBS in order to remove the MTT and the residual formazan crystals are taken up in 1 ml of DMSO. The formazan concentration for each well is read by photometry at a wavelength of 550 nm and compared with a control corresponding to medium incubated in the presence of MTT but in the absence of cells.

Figure 1A:
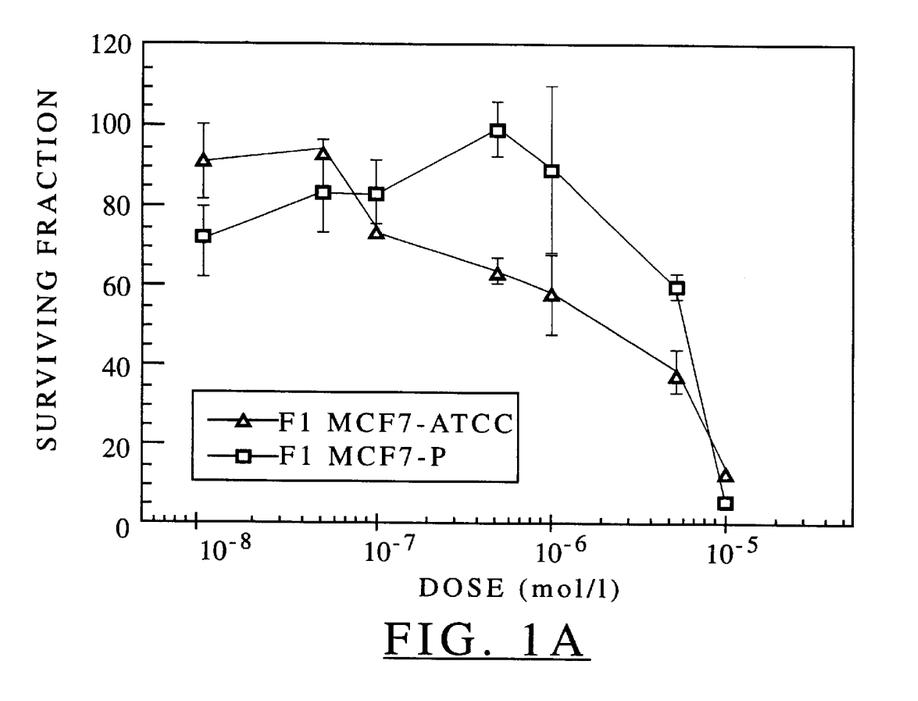
FIGS. 1A, 1B and 2 show the results of the cytotoxicity tests carried out respectively with the two isomers of a metallocene derivative in accordance with the Invention and tamoxifen.
Figure 1B:
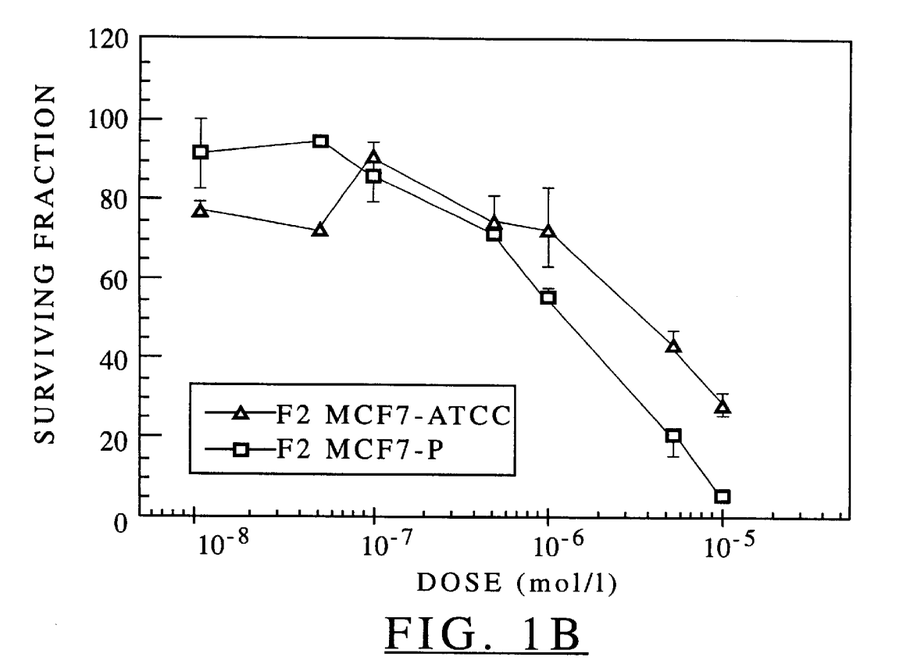

FIGS. 1A and 1B show the results of the cytotoxicity tests carried out respectively with the "cis" isomer (FIG. 1A) and the "trans" isomer (FIG. 1B) of 1-[4-(2-dimethylaminoethoxy)phenyl]-1-(4-hydroxyphenyl)-2-ferrocenyl-1-butene on the two cell lines shown above. These results are expressed as fractions of surviving cells as a function of the doses of the compound tested.

Figure 2:
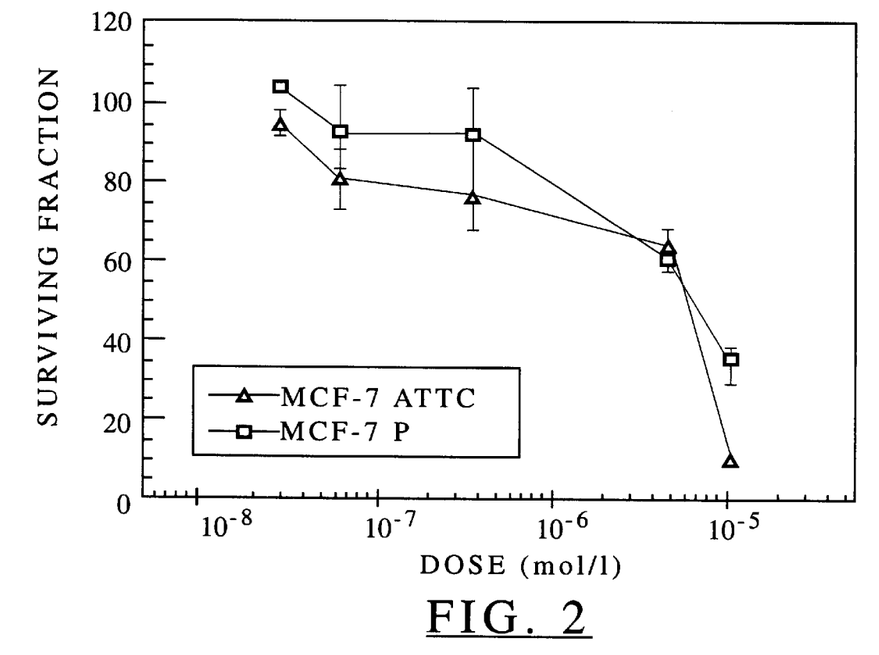

By way of comparison, FIG. 2 shows the results obtained on carrying out the same tests with tamoxifen under the same conditions.

The 50% inhibitory doses (IC50), expressed in µmol and calculated with respect to the points in FIGS. 1A, 1B and 2 between $5 \times 10^{-7}$ and $10^{-5}$ mol/l, are presented in Table 1 below.

TABLE 1

| COMPOUND TESTED | $IC_{50}$ (µmol) | |
| --- | --- | --- |
|  | MCF7 ATCC | MCF7-P |
| "Cis" derivative | 3.4 | 5.6 |
| "Trans" derivative | 4.9 | 2 |
| Tamoxifen | 6.4 | 7.2 |

The lower the 50% inhibitory dose, the greater the cytotoxic activity and the results expressed in Table 1 show that the "cis" and "trans" isomers of 1-[4-(2-dimethylaminoethoxy)phenyl]-1-(4-hydroxy-phenyl)-2-ferrocenyl-1-butene exhibit, with respect to the two cell lines tested, a cytotoxic activity which is greater than that of tamoxifen.

As emerges from the above, the Invention is in no way limited to those of its implementation, production and application methods which have just been described more explicitly; on the contrary, it encompasses all the variations thereof which can come to the mind of an expert on the subject, without departing from the context or from the scope of the present Invention.

We claim:

1. A compound of general formula (I):

$$R_5R_4C=CR_3-\text{[phenyl]}-O-(CH_2)_nZ \quad (I)$$

wherein:
the $-O(CH_2)_nZ$ group is in the meta or para position with respect to the $-CR_3=CR_4R_5$ group,
n represents an integer of between 2 and 10,
Z represents a basic or polar ligand chosen from $-NR_1R_2$ groups wherein $R_1$ and $R_2$, which are identical or different, represent a $C_1$ to $C_6$ alkyl group optionally substituted by one or a number of halogen atoms, heterocyclic groups containing a nitrogen atom or $-OR_1$, $-SR_1$, $-SOR_1$ or $-SO_2R_1$ groups wherein $R_1$ has the same meaning as above, and wherein:
either $R_3$ represents a phenyl group optionally substituted by one or a number of hydrogen atoms or halogen atoms or hydroxyl groups or $C_1$ to $C_3$ alkyl or alkoxy groups and $R_5$ represents a metallocene) group, whereas $R_4$ represents a hydrogen atom or a halogen atom or an $NO_2$ group or a chloroethyl group or a CN group or alternatively a $C_1$ to $C_3$ alkyl group, the end carbon of which can optionally be bonded to the carbon situated at the 2 position of the phenyl group of $R_3$,
or $R_3$ represents a metallocene group and $R_5$ represents a phenyl group optionally substituted by one or a number of hydrogen atoms or halogen atoms or hydroxyl groups or $C_1$ to $C_3$ alkyl or alkoxy groups, whereas $R_4$ represents a hydrogen atom or a halogen atom or an $NO_2$ group or a chloroethyl group or a CN group or alternatively a $C_1$ to $C_3$ alkyl group, in all its stereoisomeric forms and its salts.

2. The compound as claimed in claim 1, wherein the metallocene group corresponds to the general formula (II):

$$\text{(II): two cyclopentadienyl rings bonded to M}$$

wherein M represents a metal atom from Group VIII of the Periodic Classification of the chemical elements, it being possible for said atom optionally to be in an oxidized form.

3. The compound as claimed in claim 1, wherein the metallocene group corresponds to the general formula (III):

$$\text{(III): bent metallocene with M and two X ligands}$$

wherein:
M represents a metal atom chosen from titanium, vanadium, niobium, hafnium or molybdenum,
X represents a halogen atom chosen from chlorine, bromine or iodine.

4. The compound as claimed in claim 1 or claim 2, wherein it corresponds to the specific formula (I-a):

wherein:

the —O(CH$_2$)$_2$Z group is in the para position with respect to the —CR$_3$=CR$_4$R$_5$ group, Z represents an —NR$_1$R$_2$ group wherein R$_1$ and R$_2$, which are identical or different, represent a methyl group or an ethyl group or alternatively Z represents an N-pyrrolidino group, R$_3$ represents a phenyl group optionally substituted by a hydroxyl group or by a methoxy group, R$_4$ represents a hydrogen atom or a halogen atom or an NO$_2$ group or a chloroethyl group or a CN group or alternatively an ethyl group, and M represents a metal atom chosen from iron, ruthenium or osium, optionally in its oxidized form.

5. The compound as claimed in claim 4, wherein R$_1$ and R$_2$ represent a methyl group, R$_3$ represents a phenyl group substituted in the para position by a hydroxyl group and R$_4$ represents an ethyl group, this compound corresponding to the specific formula (I-a1).

6. The compound as claimed in claim 5, wherein it is [4-(2-dimethylaminoethoxy)phenyl]-1-(4-hydroxy-pheynl)-2-ferrocenyl-1-butene.

7. The compound as claimed in claim 6, wherein it is the "trans" isomer of 1-[4-(2-dimethylamino-ethoxy)phenyl]-1-(4-hydroxyphenyl)-2-ferrocenyl-1-butene.

8. The compound as claimed in claim 4, wherein R$_1$ and R$_2$ represent a methyl group, R$_3$ represents a phenyl group and R$_4$ represents an ethyl group, this compound corresponding to the specific formula (I-a2).

9. The compound as claimed in claim 8, wherein it is [4-(2-dimethylaminoethoxy)phenyl]-1-phenyl-2-ferrocenyl-1phyenyl-1-butene.

10. The compound as claimed in claim 1 wherein:

the —O(CH$_2$)$_n$Z group is in the para position with respect to the —CR$_3$=CR$_4$R$_5$ group, n is equal to 2 and Z represents an N-pyrrolidino group,

R$_3$ represents a phenyl group substituted in the para position by a hydroxyl or C$_1$ to C$_3$ alkoxy group, whereas R$_4$ represents a C$_2$ alkyl group, the end carbon of which is bonded to the carbon situated in the 2 position of the phenyl group of R$_3$, M represents a metal atom chosen from iron, ruthenium or osmium, optionally in its oxidized form, this compound corresponding to the specific formula (I-b).

11. A process for the preparation of the compound as claimed in any one of claim 1, which comprises:

a) reacting a compound of general formula (IV):

wherein:

the —O(CH$_2$)$_n$Z group is in the meta or para position with respect to the —CR$_3$=CR$_4$R$_5$ group, n represents an integer of between 2 and 10, Z represents a basic or polar ligand chosen from —NR$_1$R$_2$ groups wherein R$_1$ and R$_2$, which are identical or different, represent a C$_1$ to C$_6$ alkyl group optionally substituted by one or a number of halogen atoms, heterocyclic groups containing a nitrogen atom or —OR$_1$, —SR$_1$, —SOR$_1$ or —SO$_2$R$_1$ groups wherein R$_1$ has the same meaning as above, and wherein:

either R$_3$ represents a phenyl group optionally substituted by one or a number of hydrogen atoms or halogen atoms or hydroxyl groups or C$_1$ to C$_3$ alkyl or alkoxy groups and R$_5$ represents a bromine atom, whereas R$_4$ represents a hydrogen atom or a halogen atom or an NO$_2$ group or a chloroethyl group or a CN group or alternatively a C$_1$ to C$_3$ alkyl group, the end carbon of which can optionally be bonded to the carbon situated at the 2 position of the phenyl group of R$_3$, or R$_3$ represents a bromine atom and R$_5$ represents a phenyl group optionally substituted by one or a number of hydrogen atoms or halogen atoms or hydroxyl groups or C$_1$ to C$_3$ alkyl or alkoxy groups, whereas R$_4$ represents a hydrogen atom or a halogen atom or an NO$_2$ group or a chloroethyl group or a CN group or alternatively a C$_1$ to C$_3$ alkyl group, with a cyclopentadienyl metal salt, in order to substitute the bromine atom by a cyclopentadiene group;

b) reacting the compound obtained in Stage a) with a strong base, in order to form a cyclopentadienyl anion, c) reacting the compound obtained in Stage b) with an organometallic compound of formula: Cp—M—(CO)$_2$—X, wherein Cp represents a cyclopentadiene group, M represents a metal atom from Group VIII of the Periodic Classification of the chemical elements and X represents a halogen atom chosen from chlorine, bromine or iodine, or with an organometallic compound of formula: Cp—M—X$_m$, wherein Cp and X have the same meaning as above, M is a metal atom chosen from titanium, vanadium, niobium, hafnium or molybdenum and m is an integer equal to 3 or 4.

12. A process for the preparation of the compound of specific formula (I-a1) as claimed in claim 5, which comprises:

a) subjecting a metallocene ester of formula (V):

wherein M represents a metal atom chosen from iron, ruthenium or osmium, to an addition reaction with the organolithium compound CH₃—O—C₆H₄—Li or an organomagnesium compound of formula: CH₃—O—C₆H₄—MgX, wherein X represents a chlorine, bromine or iodine atom, which results in the formation of an intermediate alcohol, followed by a dehydration reaction of said alcohol, b) subjecting the compound obtained in Stage a) to a demethylation reaction, c) subjecting the compound obtained in Stage b) to a alkylation reaction with sodium ethoxide and the hydrochloride of 2-dimethylaminoethyl chloride.

13. The preparation process as claimed in claim 12, wherein it comprises the prior preparation of the metallocene ester of formula (V) by esterification of the corresponding metallocenylacetic acid, followed by an alkylation reaction of the carbon in the position α to the metallocenyl ring of said ester.

14. The preparation process as claimed in claim 12, wherein it additionally comprises a stage of separation of the "cis" and "trans" isomers of the co und of specific formula (I-a1) obtained.

15. A process for the preparation of the compound of specific formula (I-a2) as claimed in claim 8, which comprises:

a) reacting a metallocenic acid chloride of formula (VI):

wherein M represents a metal atom chosen from iron, ruthenium or osmium, with diphenylzinc, in order to substitute the chlorine atom by a phenyl group, b) subjecting the compound obtained in Stage a) to an addition reaction with the organolithium compound (CH₃)₂—N—(CH₂)₂—O—C₆H₄—Li or an organomagnesium compound of formula: (CH₃)₂—N—(CH₂)₂—O—C₆H₄—MgX, wherein X represents a halogen atom chosen from chlorine, bromine or iodine, which results in the formation of an intermediate alcohol, followed by a dehydration reaction of said alcohol.

16. The preparation process as claimed in claim 15, wherein it comprises in addition a stage of separation of the "cis" and "trans" isomers of the compound of specific formula (I-a2) obtained.

17. A process for the preparation of the compound of specific formula (I-b) as claimed in claim 10, which comprises:

a) reacting a tetralone of formula (VII):

wherein R₆ represents a hydrogen atom or a C₁ to C₃ alkyl group, with the organolithium compound or an organomagnesium compound of formula:

wherein X represents a halogen atom chosen from chlorine, bromine or iodine, which results in the formation of an intermediate alcohol, followed by a dehydration reaction of said alcohol;

b) subjecting the compound obtained in Stage a) to a bromination reaction, in order to obtain the compound of formula (VIII):

c) subjecting the compound of formula (VIII) thus obtained to a coupling reaction with an organometallize compound of formula: Cp—M—(C₅H₄)—Y, wherein Cp represents a cyclopentadiene group, M represents a metal atom chosen from iron, ruthenium or osmium and Y represents a lithium atom, a copper atom, an SnBu₃ group or an HgCl group.

18. A pharmaceutical composition, wherein it contains at least one of the compounds of formula (I) as claimed in any one of claim 1 or one of its salts, optionally in combination with a pharmacologically acceptable vehicle.

19. A method of combatting a tumor in a subject in need of such treatment, comprising administering to said subject a compound of formula I:

wherein:
the —O(CH₂)ₙZ group is in the meta or para position with respect to the —CR₃=CR₄R₅ group,
n represents an integer of between 2 and 10,
Z represents a basic or polar ligand chosen from —NR₁R₂ groups wherein R₁ and R₂, which are identical or different, represent a $C_1$ to $C_6$ alkyl group optionally substituted by one or a number of halogen atoms, heterocyclic groups containing a nitrogen atom or —$OR_1$, —$SR_1$, —$SOR_1$ or —$SO_2R_1$ groups wherein $R_1$ has the same meaning as above, and wherein:

either $R_3$ represents a phenyl group optionally substituted by one or a number of hydrogen atoms or halogen atoms or hydroxyl groups or $C_1$ to $C_3$ alkyl or alkoxy groups and $R_5$ represents a metallocene group, whereas $R_4$ represents a hydrogen atom or a halogen atom or an $NO_2$ group or a chloroethyl group or a CN group or alternatively a $C_1$ to $C_3$ alkyl group, the end carbon of which can optionally be bonded to the carbon situated at the 2 position of the phenyl group of $R_3$, or $R_3$ represents a metallocene group and $R_5$ represents a phenyl group optionally substituted by one or a number of hydrogen atoms or halogen atoms or hydroxyl groups or $C_1$ to $C_3$ alkyl or alkoxy groups, whereas $R_4$ represents a hydrogen atom or a halogen atom or an $NO_2$ group or a chloroethyl group or a CN group or alternatively a $C_1$ to $C_3$ alkyl group, in all its stereoisomeric forms or a physiologically acceptable salt thereof in an amount effective to combat a tumor.

20. The method as claimed in claim 19, wherein said tumor comprises estrogen-dependent tumors of the breast.

21. The method as claimed in claim 19, wherein the metallocene group corresponds to the general formula (II):

(II)

wherein M represents a metal atom from Group VIII of the Periodic Classification of the chemical elements, it being possible for said atom optionally to be in an oxidized form.

22. The method as claimed in claim 19, wherein the metallocene group corresponds to the general formula (III):

(III)

wherein:

M represents a metal atom chosen from titanium, vanadium, niobium, hafnium or molybdenum, X represents a halogen atom chosen from chlorine, bromine or iodine.

23. The method as claimed in claim 19, wherein said compound corresponds to the specific formula (I-a):

(I-a)

wherein:

the —$O(CH_2)_nZ$ group is in the para position with respect to the —$CR_3$=$CR_4R_5$ group, Z represents an —$NR_1R_2$ groups wherein $R_1$ and $R_2$, which are identical or different, represent a methyl group or an ethyl group or alternatively Z represents an N-pyrrolidino group, $R_3$ represents a phenyl group optionally substituted by a hydroxyl group or by a methoxy group, $R_4$ represents a hydrogen atom or a halogen atom or an $NO_2$ group or a chloroethyl group or a CN group or alternatively an ethyl group, and M represents a metal atom chosen from iron, ruthenium or osmium, optionally in its oxidized form.

24. The method as claimed in claim 19, wherein $R_1$ and $R_2$ represent a methyl group, $R_3$ represents a phenyl group substituted in the para position by a hydroxyl group and $R_4$ represents an ethyl group, this compound corresponding to the specific formula (I-a1).

25. The method as claimed in claim 24, wherein said compound is 1-[4-(2-dimethylaminoethoxy)phenyl]-1-(4-hydroxyphenyl)-2-ferrocenyl-1-butene.

26. The method as claimed in claim 25, wherein said compound is the "trans" isomer of 1-[4-(2-dimethylaminoethoxy)phenyl]-1-(4-hydroxyphenyl)-2-ferrocenyl-1-butene.

27. The method as claimed in claim 23, wherein $R_1$ and $R_2$ represent a methyl group, $R_3$ represents a phenyl group and $R_4$ represents an ethyl group, this compound corresponding to the specific formula (I-a2).

28. The method as claimed in claim 27, wherein said compound is 1-[4-(2-dimethylaminoethoxy)phenyl]-1-phenyl-2-ferrocenyl-1-butene.

29. The method as claimed in claim 19, wherein:

the —$O(CH_2)_nZ$ group is in the para position with respect to the —$CR_3$=$CR_4R_5$ group, n is equal to 2 and Z represents an N-pyrrolidino group, $R_3$ represents a phenyl group substituted in the para position by a hydroxyl or $C_1$ or $C_3$ alkoxy group, whereas $R_4$ represents a $C_2$ alkyl group, the end carbon of which is bonded to the carbon situated in the 2 position of the phenyl group of $R_3$, M represents a metal atom chosen from iron, ruthenium or osmium, optionally in its oxidized form, this compound corresponding to the specific formula (I-b).

* * * * *

UNITED STATES PATENT AND TRADEMARK OFFICE
CERTIFICATE OF CORRECTION

PATENT NO. : 5,863,911
DATED : January 26, 1999
INVENTOR(S) : Jaouen et al.

It is certified that error appears in the above-identified patent and that said Letters Patent is hereby corrected as shown below:

Column 14, line 22, after "metallocene" cancel the parenthesis.

Column 15, lines 40 and 50, "[4-(2-dimethylaminoethoxy)phenyl]", each occurence, should read --1-[4-(2-dimethylaminoethoxy)phenyl]--; line 50 and 51, "2-ferrocenyl-1phyenyl-1-butene." should read --2-ferrocenyl-1-butene.--; last line, cancel "any one of".

Column 17, line 21, "co und" should read --compound--; in Formula VII, "$R_5$" should read --$R_6$--.

Column 18, in Formula VIII "$R_5$" should read --$R_6$--; line 42, "organometallize" should read --organometallic--; lines 49-50, cancel "any one of".

Signed and Sealed this

Thirteenth Day of July, 1999

*Attest:*

Q. TODD DICKINSON

*Attesting Officer*

Acting Commissioner of Patents and Trademarks